(12) United States Patent
Soza et al.

(10) Patent No.: US 11,402,453 B2
(45) Date of Patent: Aug. 2, 2022

(54) METHOD AND SYSTEM FOR DETERMINING SUFFICIENCY OF MEASUREMENT DATA FOR POST-PROCESSING PROCESS

(71) Applicant: Siemens Healthcare GmbH, Erlangen (DE)

(72) Inventors: Grzegorz Soza, Heroldsberg (DE); Sebastian Schmidt, Weisendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 55 days.

(21) Appl. No.: 15/723,242

(22) Filed: Oct. 3, 2017

(65) Prior Publication Data

US 2018/0100907 A1    Apr. 12, 2018

(30) Foreign Application Priority Data

Oct. 12, 2016 (DE) .......................... 102016219887.4

(51) Int. Cl.
*G01R 33/54* (2006.01)
*A61B 6/00* (2006.01)
(Continued)

(52) U.S. Cl.
CPC ............ *G01R 33/543* (2013.01); *A61B 5/055* (2013.01); *A61B 6/032* (2013.01); *A61B 6/5264* (2013.01); *A61B 6/54* (2013.01); *A61B 6/545* (2013.01); *A61B 8/5276* (2013.01); *A61B 8/54* (2013.01); *G01R 33/5608* (2013.01); *G01R 33/56308* (2013.01); *G06T 7/0014* (2013.01); *A61B 5/7207* (2013.01); *A61B 6/503* (2013.01);
(Continued)

(58) Field of Classification Search
None
See application file for complete search history.

(56) References Cited

U.S. PATENT DOCUMENTS 5,235,510 A     8/1993   Emat
5,878,746 A *   3/1999   Lemelson ............. G06F 19/321
                                                 600/407

(Continued)

FOREIGN PATENT DOCUMENTS

DE        102015204449 A1     9/2016

*Primary Examiner* — Douglas X Rodriguez
(74) *Attorney, Agent, or Firm* — Harness, Dickey & Pierce, P.L.C.

(57) ABSTRACT

A method is for using measurement data of an object of examination for a post-processing process. In an embodiment, the method includes recording first measurement data, the first measurement data being previously determined via a medical imaging modality; automatically analyzing the first measurement data based on defined criteria and automatically inspecting a set of control parameters with aid of an analysis of the first measurement data using defined criteria with regard to second measurement data, the second measurement data being previously recorded via the modality using the set of control parameters, wherein the defined criteria include at least one of a post-processing capacity and identification of at least one image characteristic; and using at least one of the first measurement data and the second measurement data in a post-processing process. A control device and a medical imaging system are also disclosed.

35 Claims, 4 Drawing Sheets

(51) Int. Cl.
    *A61B 5/055*       (2006.01)
    *A61B 6/03*        (2006.01)
    *A61B 8/08*        (2006.01)
    *A61B 8/00*        (2006.01)
    *G01R 33/56*       (2006.01)
    *G01R 33/563*      (2006.01)
    *G06T 7/00*        (2017.01)
    *A61B 5/00*        (2006.01)
    *G01N 23/046*      (2018.01)

(52) U.S. Cl.
    CPC ............ *G01N 23/046* (2013.01); *G06T 2207/10081* (2013.01); *G06T 2207/10088* (2013.01); *G06T 2207/10132* (2013.01); *G06T 2207/20081* (2013.01); *G06T 2207/30168* (2013.01)

(56) References Cited

U.S. PATENT DOCUMENTS

| | | | |
|---|---|---|---|
| 2007/0008172 A1* | 1/2007 | Hewett | A61B 5/00 340/870.38 |
| 2010/0040268 A1* | 2/2010 | Boeing | A61B 6/482 382/128 |
| 2011/0257919 A1* | 10/2011 | Reiner | G06F 19/321 702/81 |
| 2016/0262714 A1 | 9/2016 | Krauss | |
| 2016/0350919 A1* | 12/2016 | Steigauf | G06T 7/0014 |

* cited by examiner

METHOD AND SYSTEM FOR DETERMINING SUFFICIENCY OF MEASUREMENT DATA FOR POST-PROCESSING PROCESS

PRIORITY STATEMENT

The present application hereby claims priority under 35 U.S.C. § 119 to German patent application number DE 102016219887.4 filed Oct. 12, 2016, the entire contents of which are hereby incorporated herein by reference.

FIELD

At least one embodiment of the invention generally relates to a method for using measurement data, a control device and/or a medical imaging system.

BACKGROUND

With imaging methods such as Computed Tomography (CT) or Magnetic Resonance Imaging (MRT), after acquisition the images are reconstructed from raw data and then often postprocessed. Post-processing may consist of quite simple processes such as, for example, the generation of multiplanar (MPR) and curved-planar reformatting (CPR). Increasingly, however, complicated image-based algorithmic evaluations are being used, such as for example, bone removal, volumetry of organs such as liver, lung, spleen, etc., through to perfusion evaluation, tissue classification (e.g. via dual energy), CAD (computer aided detection) to find lesions or simulation methods, e.g. from the area of flow simulation (ctFFR, fractional flow reserves calculated from CT images). These image-based methods often produce quantitative results (e.g. FFR, volumetry) or "scores", i.e. evaluations on a scale with arbitrary units e.g. for the probability of malignancy.

A frequent problem is that the recorded images are not suitable for post-processing, or only to a limited extent, as a result of artifacts. The reasons for this are numerous: motion artifacts, obesity, the patient has metal implants, stents and much more.

Often it also only transpires during the examination that certain post-processing is necessary—either due to incidental findings or due to an atypical symptom in the case of an illness. For example, in the case of an atypical pulmonary coin lesion, a texture analysis may be useful but this requires a higher dose of radiation than is usually employed for the primary examination. A further clinical example is an embolism as an incidental finding. Furthermore, certain post-processing may necessitate the addition of contrast agent during recording.

As post-processing normally only takes place after the actual examination currently, these problems are only discovered when the patient is no longer in the modality and may have already left the medical office or radiology department. In this case, he must be recalled, which is an inefficient use of time. In addition, the missing or inadequately acquired image areas cannot simply be "re-measured" because in the second examination the patient regularly lies or is positioned differently and the images do not correspond as a result. Therefore, as a rule, a completely new acquisition must be performed, possibly with additional radiation exposure.

Hitherto a visual inspection was performed by the operating personnel to assess the suitability of the acquired images for post-processing. Unfortunately, artifacts which hamper or make post-processing impossible cannot always be detected with the naked eye. Furthermore, the scanner operators are not usually radiologists and accordingly they are not trained to detect incidental findings either.

SUMMARY

At least one embodiment of the present invention specifies a method and/or a control device for using measurement data of an object of examination which efficiently enable post-processing.

At least one embodiment is directed to a method for positioning, a method for determining a posture, a control device and/or by a medical imaging system.

At least one embodiment of the method for using measurement data of an object of examination for a post-processing process includes at least the following. First measurement data, determined via a medical imaging modality, is recorded. Next, an automatic analysis of the first measurement data takes place on the basis of defined criteria. Here, optionally, an automatic inspection of a set of control parameters also takes place, wherein the first measurement data is analyzed using defined criteria with regard to second measurement data which was recorded via the modality using the set of control parameters. Both in the analysis of the first measurement data as well as in the analysis of the first measurement data for inspecting the set of control parameters, the defined criteria comprise a post-processing capacity of the measurement data and/or an identification at least one image characteristic. Next, again optionally, the set of control parameters is modified. Further optionally, second measurement data is then recorded using the set of control parameters, modified if need be. Finally, the first measurement data and/or the second measurement data is used in a post-processing process.

In an embodiment, the aforementioned control device for using measurement data of an object of examination for a post-processing process comprises an acquisition unit, an analysis unit, a post-processing unit and optionally a modification unit. The control device is designed such that it performs the steps of the method according to the invention for using measurement data.

In an embodiment, the control device for using measurement data of an object of examination for a post-processing process comprises an acquisition unit to record first measurement data and second measurement data, determined via a medical imaging modality; a memory configured to store computer-readable instructions; and a processor configured to execute the computer-readable instructions to automatically analyze the first measurement data with regard to a post-processing capacity based on defined criteria and to automatically inspect a set of control parameters with aid of the analyzing of the first measurement data, and to use the first measurement data in the post-processing process.

In an embodiment, the medical imaging system comprises a control device according to at least one embodiment of the invention and a medical imaging modality. The medical imaging modality can, as aforementioned, be a CT device, an MRT device, a tomosynthesis device, an ultrasound device or an angiography unit.

In particular, the control device according to at least one embodiment of the invention can be part of a user terminal or of a computer system of a medical imaging system of at least one embodiment.

A realization which largely comprises software has the advantage that control devices used hitherto can easily be upgraded to work in the manner according to the invention by way of a software update. Inasmuch, at least one embodiment is directed to a non-transitory computer program product (such as a computer readable medium for example) with a computer program which can be loaded directly into a storage device of a control device of a medical imaging system, with control sections to perform at least one embodiment of the method according to the invention when the program is executed in the control device. In addition to the computer program, such a computer program product may also possibly comprise additional components such as, for example, documentation and/or additional components, as well as hardware components such as, for example, dongles, etc. for use of the software.

BRIEF DESCRIPTION OF THE DRAWINGS

Hereinafter, the invention is explained in more detail once again with reference to the attached figures using example embodiments. In the various figures, identical components are given identical reference numbers. The figures are not to scale as a rule. In the figures.

DETAILED DESCRIPTION OF THE EXAMPLE EMBODIMENTS

Figure 1:
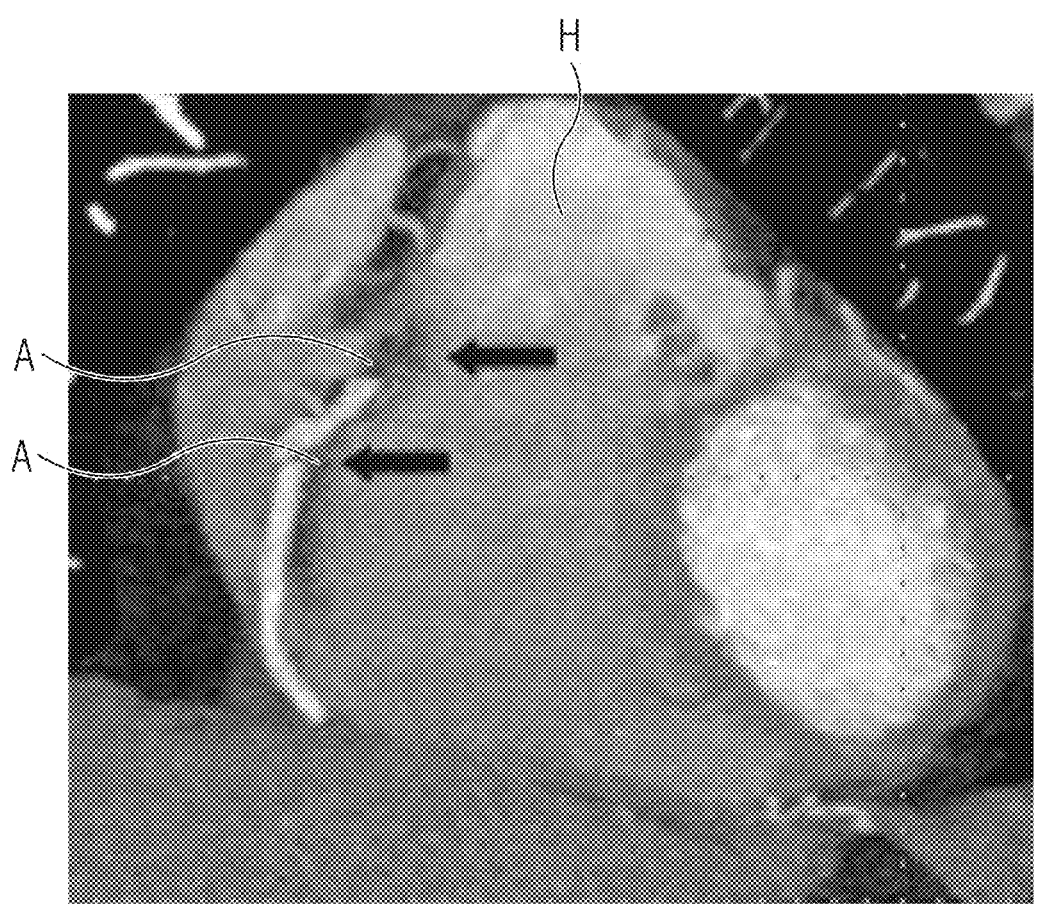
FIG. 1 shows a CT scan of a heart with a movement artifact.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above.

Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the method for using measurement data of an object of examination for a post-processing process includes at least the following. First measurement data, determined via a medical imaging modality, is recorded. Next, an automatic analysis of the first measurement data takes place on the basis of defined criteria. Here, optionally, an automatic inspection of a set of control parameters also takes place, wherein the first measurement data is analyzed using defined criteria with regard to second measurement data which was recorded via the modality using the set of control parameters. Both in the analysis of the first measurement data as well as in the analysis of the first measurement data for inspecting the set of control parameters, the defined criteria comprise a post-processing capacity of the measurement data and/or an identification at least one image characteristic. Next, again optionally, the set of control parameters is modified. Further optionally, second measurement data is then recorded using the set of control parameters, modified if need be. Finally, the first measurement data and/or the second measurement data is used in a post-processing process.

The measurement data may comprise, for example, topogram data, raw data or image data. Topogram data refers to the data of a topogram created as an overview image which was recorded via the medical imaging modality. It usually produces a two-dimensional image of the object of examination. The raw data refers to unprocessed data. It is therefore the data which is recorded from the inside of the object of examination in the context of image acquisition. From it, a three-dimensional volume data set can subsequently be reconstructed as image data of the object of examination. The object of examination can in principle involve arbitrary objects and/or living beings but the object of examination is preferably a human patient.

The measurement data is used for the post-processing process, which is also referred to as post-processing hereinafter. This can, as aforementioned, comprise simple processing such as, for example, the creation of a multiplanar or curved-planar reformatting. In the context of post-processing, however, complicated image-based algorithmic evaluations can also be undertaken, e.g. the bones can be removed from the image (bone removal). Furthermore, liver, lungs, spleen etc. can be volumetrically examined. Moreover, a perfusion evaluation, i.e. an evaluation of the perfusion of a hollow organ, or a tissue classification can be undertaken. Furthermore, a CAD algorithm to detect lesions can be applied to the measurement data or calculated by way of a simulation method e.g. a flow simulation such as ctFFR, in other words, from a fractional flow reserve calculated from CT images.

The kind of post-processing process can, for example, be determined by a user or determined automatically on the basis of an indication which is noted in an associated, possibly digital, patient file. The method according to the invention is used to determine whether and to what extent the measurement data can be used for the desired post-processing process. This is explained in more detail hereinafter on the basis of the individual steps of the method.

First of all, first measurement data, which need not necessarily be data which is suitable for a 3-D reconstruction, is recorded. Thus, for example, this may also be two-dimensional topogram data. The measurement data was acquired in advance via the modality as part of a customary acquisition method (CT scan, MRT sequence etc.) known to a person skilled in the art using a control protocol or a set of control parameters. This can therefore take place, for example, with a CT device, an MRT device, an ultrasound device, an angiography unit or the like for the modalities suitable for three-dimensional imaging. In the control protocol—also referred to as an examination protocol—the temporal sequence and further control parameters, preferably all those required for acquisition, are predefined. As a result, acquisition can be performed automatically or semi-automatically.

The following analysis takes place at least semi-automatically but preferably fully automatically. Although it may also comprise variables to be calculated from the measurement data such as signal-to-noise ratio, contrast-to-noise ratio, image sharpness and the like, preferably however, a complex analysis of the measurement data is undertaken on a scale and using means such as those provided, for example, by machine learning. As part of the analysis, first measurement data is examined on the basis of defined criteria which, for example, is determined in the context of a prior learning method using patient-specific data, by way of user input or the like.

Optionally, an automatic inspection of a set of control parameters can also take place in the context of this step. The set of control parameters comprises, for example, a control protocol which was used for the acquisition of the first measurement data. Therefore, the terms "set of control parameters" and "control protocol" are also used synonymously hereinafter. Customarily, a control protocol or a set of control parameters is selected from a number of predefined control protocols. On the one hand, this can be done automatically on the basis of an indication or on the other hand, the selection can be made by a user. Alternatively, the set of control parameters can also be manually adjusted by a user and thus predetermined. The set of control parameters thus predetermined is examined. The examination ascertains whether second measurement data which is still to be recorded in a subsequent acquisition step is likely to be suitable for the post-processing process to be performed.

Both in the automatic analysis of the first measurement data and in the inspection of the set of control parameters, the criteria comprise a post-processing capacity and/or enable the identification of at least one image characteristic. In ascertaining the post-processing capacity, the measurement data is assessed in terms of its quality or suitability. It is therefore determined whether it meets the requirements regarding suitability and quality for successful post-processing.

In the following optional step, the second measurement data is recorded using the, if need be, modified set of control parameters. The aforementioned acquisition methods are used for this purpose such that a subsequent 3D-reconstruction is enabled with the measurement data. For use in the post-processing process, the measurement data, in other words, the first measurement data and/or the second measurement data, can be combined, for example, to reduce the image noise, as subsequently explained in more detail.

The method according to at least one embodiment of the invention therefore enables the analysis, inspection or assessment of recorded measurement data in order to decide whether and to what extent the measurement data is used in the post-processing process and whether further measurement data should be recorded with an, if need be, modified set of control parameters. However, in contrast to the known prior art, this takes place before the post-processing process and by way of a complex analysis using defined criteria which exceed simple variables such as the signal-to-noise ratio (SNR), contrast-to-noise ratio (CNR) etc. Therefore, abstracted criteria which cannot be directly calculated from the image data are preferably taken into account.

In an embodiment, the aforementioned control device for using measurement data of an object of examination for a post-processing process comprises an acquisition unit, an analysis unit, a post-processing unit and optionally a modification unit. The control device is designed such that it performs the steps of the method according to the invention for using measurement data.

The aforementioned medical imaging system comprises a control device according to at least one embodiment of the invention and a medical imaging modality. The medical imaging modality can, as aforementioned, be a CT device, an MRT device, a tomosynthesis device, an ultrasound device or an angiography unit.

The essential components of the control device according to at least one embodiment of the invention can be designed, for the most part, in the form of software components. In principle, however, these components can also be partly realized in the form of software-supported hardware, for example, FPGAs or the like—in particular, where particularly fast calculations are involved. Likewise, the required interfaces can be designed as software interfaces, for example, where only the transfer of data from other software components is involved. However, they can also be designed as hardware interfaces which are controlled by appropriate software.

In particular, the control device according to at least one embodiment of the invention can be part of a user terminal or of a computer system of a medical imaging system.

A realization which largely comprises software has the advantage that control devices used hitherto can easily be upgraded to work in the manner according to the invention by way of a software update. Inasmuch, at least one embodiment is directed to a non-transitory computer program product (such as a computer readable medium for example) with a computer program which can be loaded directly into a storage device of a control device of a medical imaging system, with control sections to perform at least one embodiment of the method according to the invention when the program is executed in the control device. In addition to the computer program, such a computer program product may also possibly comprise additional components such as, for example, documentation and/or additional components, as well as hardware components such as, for example, dongles, etc. for use of the software.

For transport to the control device and/or for storage on or in the control device, a computer-readable medium, for example, a memory stick, a hard disk or another transportable or integrated data carrier can be used, on which the control sections of the computer programs readable and executable from a processor unit of the control device are saved. The processor unit may, for example, have one or more collaborating microprocessors or the like for this purpose.

Further particularly advantageous embodiments and developments of the invention emerge from the claims and the subsequent description, wherein the independent claims can be developed to form a claim category also analogous to the dependent claims of another claim category and its description and in particular, individual features of different example embodiments or versions can also be combined to form new example embodiments or versions.

In the method according to at least one embodiment of the invention, the analysis of the first measurement data preferably comprises a machine learning method, particularly preferably based on a database of reference objects of examination. In the context of the machine learning method, part of the defined criteria is determined. In particular, this involves complex criteria with the help of which the machine or the arithmetic unit or also the computer can analyze which measurement data is better suited to the desired post-processing process and which is less suited, for example, based on an algorithm.

A preferable learning method comprises the following. Firstly, learning data, particularly preferably from the database of reference objects of examination, is recorded. The learning data can be raw data and/or image data. The learning data is subsequently—possibly after an image reconstruction from the raw data; post-processed in a post-processing process. The result of the post-processing process is inspected or assessed in a further step. The assessment can, for example, be undertaken using a grading scale, although a distinction is at least drawn between image data in which post-processing has functioned, and image data in which it has not functioned sufficiently well or at all. The assessment can be made by a processor but an automatic plausibility check which is subsequently described in more detail can also take place.

With the aid of the assessed results of the post-processing process, a discriminator (e.g. a neural network) is then trained. The discriminator distinguishes output data, i.e. learning data and/or measurement data with regard to its post-processing capacity. In addition, or alternatively, it identifies image characteristics of the output data. The discriminator is trained until a sufficient level selectivity has been achieved, i.e. until it distinguishes between the good and bad post-processing capacity of the output data with sufficient statistical probability or identifies image characteristics with sufficient probability.

The learning method is particularly preferably performed "in-line". This means that an operator evaluates result images which were generated by way of the method according to the invention for using measurement data, and thus continues to train the discriminator. The measurement data which is recorded in operation is therefore likewise to be viewed as learning data at the same time. This enables ever more precise adjustment of the discriminator, including after the initial teaching.

In a method according to at least one embodiment of the invention, the image characteristics preferably comprise object-specific image characteristics, particularly preferably obesity, lesions, embolisms, motion artifacts, metal artifacts and/or other artifacts. In contrast to device-specific image characteristics which can be traced back to inaccuracies or possible disturbances of the modality, object-specific image characteristics originate directly from the object of examination. They can be identified in the measurement data, for example, by way of a CAD algorithm (computer aided detection). The identification of these image characteristics is particularly advantageous as it is therefore possible to react to the respectively identified image characteristic with a modification of the set of control parameters for a subsequent image acquisition. This means the control parameters or the examination protocol can be individually adjusted, preferably also area by area, to the identified image characteristic.

The analysis of the first measurement data preferably comprises a plausibility check of the identification of the image characteristic. A "plausibility check" means that a probability with which the image characteristic was correctly identified is determined. For this, the identified image characteristic is compared, for example, with demographic information such as, for example, an age-disease correlation. Alternatively, or in addition, further information from an associated patient file such as, for example, the localization of metal implants, previous operations and/or the indication of the clinical picture can be used for comparison as part of the plausibility check. With the aid of the plausibility check it is therefore at least possible to automatically assess the probability with which one of the aforementioned image characteristics is present. Thus, in the course of further analysis, it is possible to decide whether additional measurement data should be recorded by way of a further acquisition step, possibly with a modified set of control parameters.

In the method according to at least one embodiment of the invention, the first measurement data and/or the second measurement data in the method according to at least one embodiment of the invention are preferably used subject to an analysis result, particularly preferably subject to its post-processing capacity. Therefore, particularly preferably an analysis of the second measurement data is also performed and an analysis result including the post-processing capacity determined.

When using the measurement data, for example, on the one hand, for instance, certain image areas can only be formed from the first measurement data or the second measurement data respectively. On the other hand, the first measurement data and the second measurement data can, for example, be superimposed in a linear combination, wherein the coefficients for the linear combination are ascertained subject to the analysis results. It is also possible, for example, that the first measurement data are only poorly or not suited to the post-processing process such that only the second measurement data ascertained with the parameter set, modified where necessary, is used in the post-processing process.

Often post-processing or a subsequent diagnosis takes place with a time lag from image acquisition such that a lack of suitability of the data for post-processing or an incidental finding can also be ascertained only then. In the method according to the invention, however, after an acquisition of the first measurement data the object of examination remains in the modality at least until the analysis of the first measurement data and the optional recording of second measurement data. In other words, the object of examination is not restored and at best not moved either until it has been ensured that data with sufficient post-processing capacity has been recorded. Respectively, in the case of an incidental finding, additional data required for a diagnosis is acquired where necessary. It is thus ensured that the object of examination, hence in particular the patient, need not leave the modality and a comparison or a registration of the measurement data is thus facilitated. By this means, the most optimal measurement data possible can be provided for subsequent post-processing with the minimum expenditure of time.

In the method according to at least one embodiment of the invention, the set of control parameters comprises at least one of the following parameters: tube voltage, tube current, filtering, dual energy, reconstruction method, layer thickness, triggering, gantry tilt, pulse sequence and/or delay. The aforementioned parameters are therefore control parameters which establish essential variables for an acquisition process. Some parameters only concern certain modalities, while other parameters can similarly be applied to different modalities.

Thus, on the one hand for example, tube voltage and tube current determine parameters for the operation of an X-ray tube as used e.g. in CT devices. On the other hand, for example, the pulse sequence is a parameter which specifies variables and chronological results of magnetic fields used for the MRT in order to manipulate and then read out the spins in the object of examination. Other parameters such as, for example, layer thickness, triggering and/or delay can be applied in several modalities and are therefore not specific to one modality. The layer thickness refers to the resolution in one scan direction and the triggering determines a defined event after which image acquisition is started. The delay, in other words the delay time, determines whether and how long to wait after a defined event before starting the acquisition.

When X-rays are used, filtering determines whether and which filters should be used. Thus, for example, certain areas of a spectrum emitted by an X-ray tube can be selectively, wholly or partially completed via spectral filters or the X-rays attenuated or fully completed via a shaping filter for certain spatial areas. The dual energy parameter indicates whether two sets of measurement data using different X-ray spectra should be recorded as part of acquisition. With the "reconstruction method" parameter, it is also possible to determine which reconstruction method, hence for example, filtered rear projection or iterative image reconstruction algorithms, should be used. The "gantry tilt" parameter describes an angle between the rotational plane of the gantry and an advance direction of the object of examination, for example, in the case of a CT device.

The list of these parameters is incomplete. A person skilled in the art can therefore add further customary parameters to the set of control parameters which can likewise be modified as part of the method according to at least one embodiment of the invention. Examples of this are the pitch in a helical CT scan or the total time which is required for the complete acquisition of the measurement data.

Some of the steps of the method according to at least one embodiment of the invention are preferably repeated iteratively until a defined termination criterion is obtained. The steps to be repeated particularly preferably comprise the steps of recording, analysis and modification. Based on the analysis, for example, the set of control parameters is constantly optimized iteratively to obtain the best possible result image after the post-processing process. Accordingly, the post-processing capacity can be one of the defined termination criteria. In addition, for example, radiation exposure of the object of examination can trigger the termination of at least one embodiment of the method.

Preferably the steps of the method according to at least one embodiment of the invention are performed as part of real-time imaging. With the continual acquisition of measurement data, numerous sets of measurement data are acquired from which a three-dimensional image of the object of examination can be reconstructed respectively. Parallel to continuous data acquisition, the method according to at least one embodiment of the invention is performed for the respective current set of measurement data. Such sets of control parameters possibly modified as part of the method according to the invention can be used in this manner immediately or with a certain delay (e.g. at the start of a subsequent scan section) to determine the parameters for data acquisition. Likewise, in parallel, post-processing is performed for real-time imaging and the images obtained from this output on a suitable output device such as, for example, a screen or via a projector. For real-time imaging, the method according to the invention therefore ensures constant optimization of the image views obtained by way of post-processing which are then shown on the display unit.

As aforementioned, the first measurement data preferably comprises raw data, image data and/or topogram data.

In a version of the method according to at least one embodiment of the invention, the first measurement data preferably comprises topogram data. In this case, the optional procedural steps or optional components of the procedural steps are performed. A set of control parameters is therefore checked, as aforementioned. Furthermore, the set of control parameters is modified and second measurement data recorded using the set of control parameters.

Based on the topogram data, a control protocol or set of control parameters is therefore preferably selected from a number of predefined control protocols, as aforementioned. This set of control parameters is checked as part of the method. During checking, using the defined criteria it is ascertained on the basis of the topogram data whether second measurement data which should still be included in a subsequent acquisition step are expected to be suitable for the post-processing process to be performed. Thereupon, the set of control parameters is modified if necessary and the second measurement data acquired with this set of control parameters and finally used for the post-processing process.

Taken in isolation as purely two-dimensional data, topogram data is not suitable for three-dimensional post-processing. Therefore, in the case of this version the raw data suitable for the post-processing process or image data reconstructed from it is acquired as second measurement data by way of the set of control parameters, modified if need be.

FIG. 1 shows a CT scan of a heart H of a human patient 10 as an object of examination by way of example. Inside the heart H, areas in which a so-called stair-step artifact A can be discerned are marked with black arrows. The stair-step artifact A is attributable to an irregular movement of the heart which occurred while raw data was being acquired for subsequent image reconstruction with the aid of a CT device. As a movement artifact, the stair-step artifact A hampers post-processing processes such as, for example, segmentation. Other post-processing processes such as, for example, a flow simulation by way of ctFFR are completely impossible.

Figure 2:
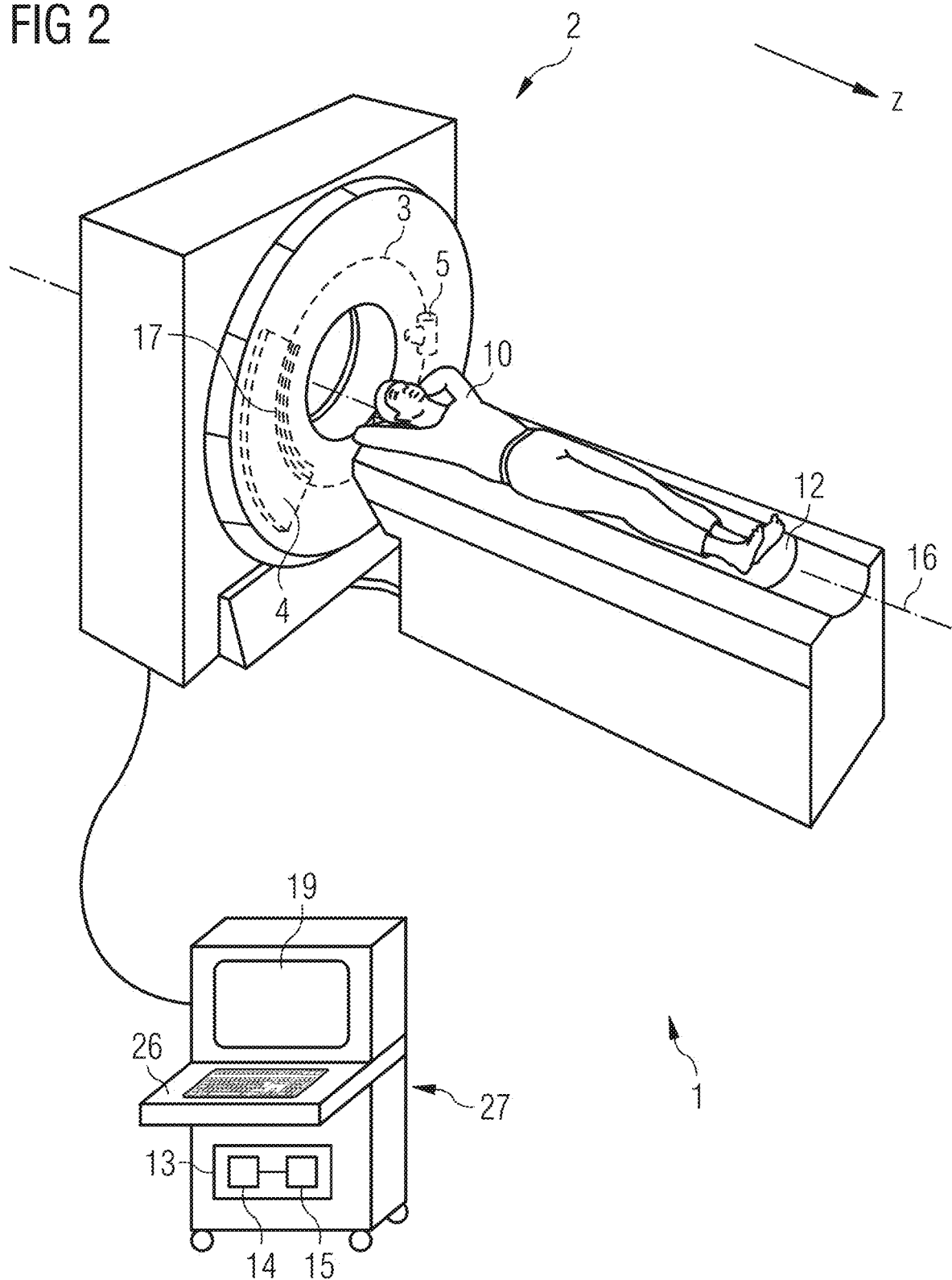
FIG. 2 shows a perspective and diagrammatic view of an example embodiment of a medical imaging system according to the invention.

By way of example and as a rough diagram, FIG. 2 shows a computed tomography system 1 as a medical imaging system according to the invention, comprising a user terminal 27 and a computed tomography device 2 as a medical imaging modality. The computed tomography system 1 is designed to perform the method according to the invention for using measurement data. The computed tomography device 2 comprises a patient table 12 for the accommodation of a patient 10 as an object of examination, which is adjustable along a system axis 16. Hereinafter the system axis 16 is also referred to as the z axis, which is adjustable with the patient 10 in the measurement field. Furthermore, it comprises a gantry 3 with a source detector arrangement 4, 5 pivoted around the system axis 16. The source detector arrangement 4, 5 has an X-ray source 5 and a detector 4 facing each other such that during operation an X-ray emanating from the focus of the X-ray source 5 hits the detector 4. For locally resolved recording of X-rays, the detector 4 is structured in individual pixels 17 which are arranged in a number of detector lines. Detectors 4 with a total of 64 or more lines and a local resolution in the submillimeter range are currently used.

The detector 4 generates a set of projection data for each projection. The projection data represents the attenuation values of all the pixels 17 of X-rays attenuated by the patient 10. It is recorded in the detector 4 and forwarded to the user terminal 27 with an arithmetic unit 13 comprising a control device 15 according to the invention and a reconstruction device 14. Depending on whether the method according to the invention is to be performed on the basis of the raw data RD or on the basis of the image data BD, the data is forwarded to the control device 15 before or after an image reconstruction via the reconstruction device 14. The control device 15 analyzes the data and then carries out corresponding post-processing, if necessary also at an interval. In doing so, a result image is generated which, for example, can be shown on a display unit 19 and/or which is filed in a storage unit and/or can be sent to other systems. The user terminal 27 also comprises a keyboard 26 as an input device with which an operator can, if necessary, adjust values for parameters for image reconstruction, for control and/or for post-processing.

As is known, such a computed tomography system 1 is used for 3-D image reconstruction. To record an image of a Region of Interest, projection data is recorded from a multiplicity of different projection directions during rotation of the source detector arrangement 4, 5. In the case of a spiral scan, during a rotation of the source detector arrangement 4, 5, for example, a continuous adjustment of the patient table 12 in the direction of the system axis 16 takes place simultaneously. With type of scanning, the X-ray source 5 and the detector 4 therefore move on a helical path around the patient 10.

Figure 3:
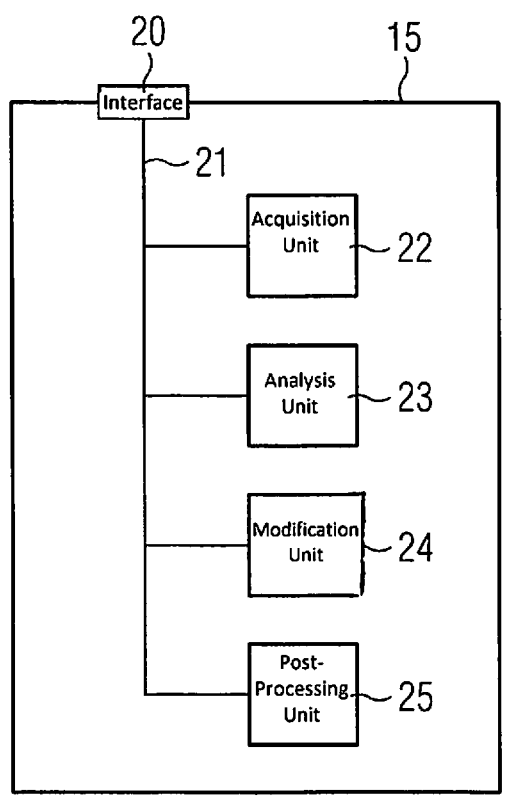
FIG. 3 shows a diagrammatic block diagram of an example embodiment of a control device according to the invention.

FIG. 3 shows a block diagram of a control device 15 according to the invention by way of example. It comprises an acquisition unit 22, an analysis unit 23, a modification unit 24 and a post-processing unit 25 which are connected via a bus 21 for data transmission. Data can therefore be freely exchanged between the components of the control device 15 by way of the bus 21. The control device 15 also comprises an interface 20 which connects it to other components of the CT system 1 such as, for example, the reconstruction device 14 or a control device for controlling the CT device 2. It is used to transfer data from the control device 15 to these components and vice versa.

Figure 4:
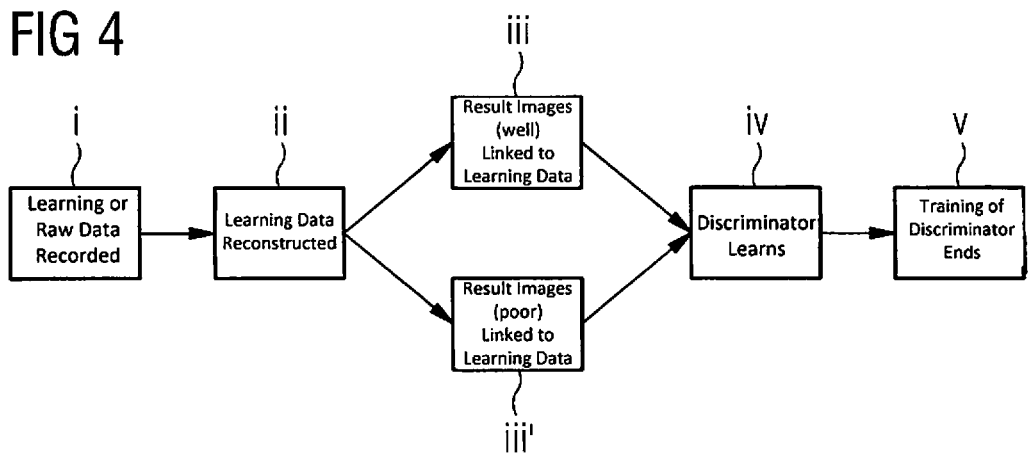
FIG. 4 shows a diagrammatic block diagram of an example embodiment of a learning method.

By way of example, FIG. 4 shows a block diagram of a learning method for training a discriminator which undertakes an analysis of measurement data in the method according to the invention for using data. In a first step i, learning data which involves a collection of image data from a database of reference objects of examination is recorded. Alternatively, in the first step i, raw data which originate directly from the acquisition process can also be recorded, but they can also be filed in a database without an image reconstruction being performed.

The learning data is reconstructed in a second step ii, if necessary, and processed to form result images as part of a post-processing process. The result images obtained are subsequently checked and evaluated. The viewer therefore decides whether the post-processed learning data provides a sufficiently good or a poor result image.

In a third step iii, the result images for which post-processing has worked well are linked to their assigned learning data. Analogously, in step iii' the result images for which post-processing has worked poorly or not at all are linked to their associated learning data. In the subsequent fourth step iv, a discriminator is trained in terms of the well-evaluated data from step iii and the poorly evaluated data from iii'. In step iv, the discriminator therefore learns on the basis of which output data good or bad post-processing is possible. In a fifth step v of the learning method, the training of the discriminator is completed when sufficient selectivity has been obtained. The selectivity indicates with which statistical reliability the discriminator makes a correct decision and can therefore be specified, for example, as a percentage or in standard deviations.

Figure 5:
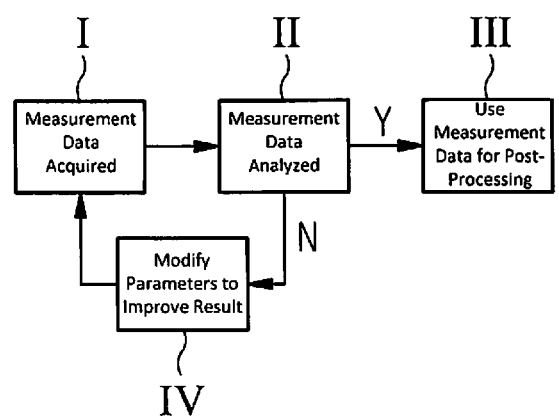
FIG. 5 shows a diagrammatic block diagram of an example embodiment of a method according to the invention for using measurement data.

FIG. 5 shows a diagrammatic view of an example embodiment of a method according to the invention as a block diagram. In a first step I, measurement data, hence raw data RD, image data BD or topogram data TD, is acquired via the CT device 2 and a set of control parameters defined by an operator. The measurement data is forwarded to the control device and recorded by the latter via the acquisition unit 22.

In the analysis unit 23, in the following step II the measurement data is analyzed, wherein the discriminator trained using the learning method from FIG. 4 decides whether the post-processing capacity is sufficient or not. In the negative case N (insufficient post-processing capacity), the set of control parameters used in step I is modified in a step IV such that a better post-processing result can be expected. With the modified set of control parameters, the method begins again with step I. However, if the positive case Y (sufficient post-processing capacity) is determined in step II, the measurement data is used directly in a step III for the post-processing process.

The steps I, II and IV can be performed consecutively in an iterative process until a defined termination criterion is obtained. This means, for example, until sufficient post-processing capacity is available and step II is continued or until, for example, a defined radiation exposure is obtained for the patient 11.

Figure 6:
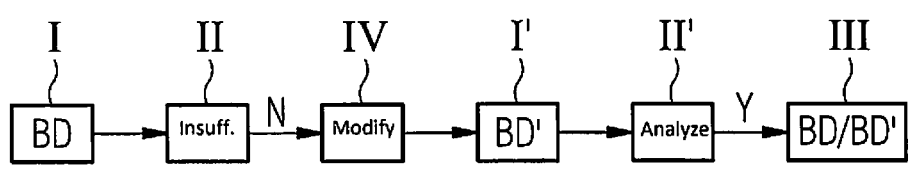
FIG. 6 shows a diagrammatic block diagram of a sequence of a method according to an embodiment of the invention.

FIG. 6 shows a specific example of a sequence according to an embodiment of the invention of the method from FIG. 5 diagrammatically in a block diagram. In step I image data is recorded with post-processing capacity which is assessed as insufficient in step II. In this negative case N, the set of control parameters in step IV is modified in the modification unit 24. Using the modified set of control parameters, via the CT device 2 the second measurement data which is recorded as second image data BD' in step I' is acquired by the control device 15. The second image data BD' is analyzed by the discriminator in step II'. Now the post-processing capacity of the image data BD' is sufficient such that in this positive case Y, the use of the first image data BD and the second image data BD' is continued in step III. In step III the image data BD and the new image data BD' is used in the post-processing unit 25 by adding it to a common result image in a post-processing process by way of a linear combination with coefficients which correspond to the post-processing capacity of the respective image data BD, BD'.

Figure 7:
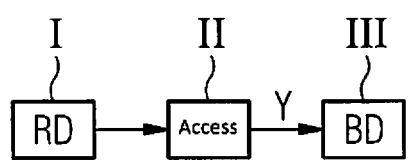
FIG. 7 shows a diagrammatic block diagram of a further sequence of a method according to an embodiment of the invention and FIG. 8 shows a diagrammatic block diagram of a further sequence of a method according to an embodiment of the invention.

In FIG. 7 a further specific example of a sequence of the method from FIG. 5 is shown diagrammatically in a block diagram. In step I raw data RD is recorded by the control device 15 as it was activated via the CT device 2. In step II the discriminator assesses the analysis unit 23 directly based on the raw data RD of its post-processing capacity. In the positive case Y, the post-processing capacity of the raw data RD is here sufficient such that step III can be continued. After a reconstruction of image data BD from the raw data RD, in step III the image data BD is used by the post-processing unit 25 for the desired processing process.

Figure 8:
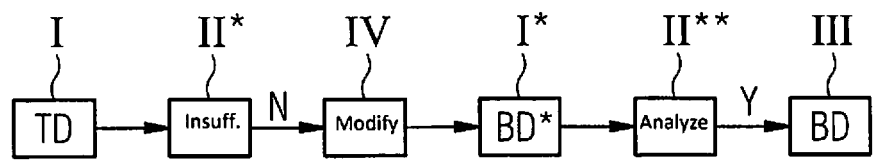

FIG. 8 shows a further sequence of the method from FIG. 5 exemplarily and diagrammatically in a block diagram. In the first step I, topogram data TD is here recorded from the acquisition unit 22. In step II*, the analysis unit 23 determines that the topogram data TD is not suitable for a post-processing process. As part of the analysis, whether suitable measurement data can be acquired by way of a predefined set of control parameters is also examined. In the present negative case (insufficient post-processing capacity), subject to the analysis from step II*, the set of control parameters is now modified by the modification unit 24. With the modified set of control parameters, via the CT device 2 new measurement data is acquired which, following a reconstruction step, is recorded as image data BD* by the control device 15 in step I*. In step II**, the image data BD* is analyzed by the analysis unit 23 with regard to its post-processing capacity. In the present positive case Y, the post-processing program of the image data BD* is sufficient as it was acquired with the already optimized set of control parameters. Accordingly, it can be used in step II for the desired post-processing process.

Finally, it is pointed out again that the devices and methods previously described in detail are only example embodiments which may be modified in many different ways by a person skilled in the art without departing from the scope of the invention. Furthermore, the use of the indefinite article "an" or "a" does not rule out the features concerned also being present several times. Likewise, the terms "device", "unit" and "system" do not rule out the component concerned consisting of several interacting subcomponents which may possibly also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method comprising:
recording first measurement data of an object of examination, the first measurement data determined via a medical imaging modality;
determining whether the first measurement data is insufficient with regard to a desired post-processing process among a plurality of post-processing processes by automatically analyzing the first measurement data using a neural network based on defined criteria, the desired post-processing process including a data modification operation or a data analysis operation, the defined criteria including at least one of a post-processing capacity of the desired post-processing process or identification of at least one image characteristic associated with the post-processing capacity, the neural network being trained based on reference measurement data of reference objects of examination, and the reference measurement data including positive reference measurement data determined to provide a sufficient result image when processed by the desired post-processing process;
obtaining, via the medical imaging modality, second measurement data of the object of examination using a modified set of control parameters in response to determining that the first measurement data is insufficient with regard to the desired post-processing process for the first measurement data, the modified set of control parameters modified based on an automatic inspection of a set of control parameters with aid of an analysis of the first measurement data using the defined criteria; and
performing the desired post-processing process using the second measurement data.

2. The method of claim 1, wherein the at least one image characteristic includes at least one object-specific image characteristic.

3. The method of claim 2, wherein the at least one object-specific image characteristic includes at least one of obesity, lesions, embolisms, motion artifacts, metal artifacts or other artifacts.

4. The method of claim 2, further comprising:
performing the desired post-processing process using the first measurement data in response to determining that the first measurement data is sufficient with regard to the desired post-processing process.

5. A non-transitory computer-readable medium including control sections, which are readable and executable by a processor unit, to perform the method of claim 2 when the control sections are executed by the processor unit.

6. The method of claim 1, wherein the automatically analyzing the first measurement data includes a plausibility check of an identification of the at least one image characteristic.

7. The method of claim 1, further comprising:
performing the desired post-processing process using the first measurement data in response to determining that the first measurement data is sufficient with regard to the desired post-processing process.

8. The method of claim 1, wherein after acquisition of the first measurement data, the object of examination remains in the medical imaging modality at least until the automatically analyzing the first measurement data is completed.

9. The method of claim 1, wherein the set of control parameters comprises at least one of tube voltage, tube current, filtering, dual energy, reconstruction method, layer thickness, triggering, gantry tilt, pulse sequence or delay.

10. The method of claim 1, wherein at least one of the recording, determining, obtaining or performing is repeated iteratively until a defined termination criterion is obtained.

11. The method of claim 10, wherein the recording, determining, obtaining and performing are performed in the context of real-time imaging.

12. The method of claim 1, wherein the recording, determining, obtaining and performing are performed in the context of real-time imaging.

13. The method of claim 1, wherein the first measurement data includes at least one of image data, raw data or topogram data.

14. The method of claim 1, wherein the first measurement data includes topogram data, and the method further comprises:
automatically inspecting the set of control parameters with the aid of the analysis of the first measurement data using the defined criteria; and
modifying the set of control parameters to obtain the modified set of control parameters.

15. A non-transitory computer program product including a computer program, which is directly loadable into a storage device of a computing device, to perform the method of claim 1 when the computer program is executed by the computing device.

16. A non-transitory computer-readable medium including control sections, which are readable and executable by a processor unit, to perform the method of claim 1 when the control sections are executed by the processor unit.

17. The method as claimed in claim 1, further comprising:
modifying the set of control parameters to obtain the modified set of control parameters.

18. The method of claim 1, wherein after acquisition of the first measurement data, the object of examination remains in the medical imaging modality at least until obtaining the second measurement data.

19. The method of claim 1, further comprising:
obtaining a selection of the desired post-processing process from among the plurality of post-processing processes.

20. The method of claim 1, wherein the neural network is trained based on the reference measurement data and an assessment, the assessment corresponding to the reference measurement data after performing the desired post-processing process on the reference measurement data.

21. The method of claim 1, wherein the desired post-processing process includes reformatting respective measurement data, segmenting a feature included in the respective measurement data, measuring the feature, classifying the feature, or performing a simulation using the respective measurement data.

22. The method of claim 1, wherein the reference measurement data includes negative reference measurement data determined to provide an insufficient result image when processed by the desired post-processing process.

23. The method of claim 1, further comprising:
processing learning data using the desired post-processing process to obtain a plurality of result images; and
linking a respective result image among the plurality of result images to corresponding learning data to obtain the positive reference measurement data in response to determining the respective result image is sufficient.

24. The method of claim 1, wherein the sufficient result image is produced when the desired post-processing process is performed successfully.

25. A control device comprising:
an acquisition unit to
record first measurement data of an object of examination, the first measurement data determined via a medical imaging modality, and
record second measurement data of the object of examination, the second measurement data obtained via the medical imaging modality using a modified set of control parameters in response to determining that the first measurement data is insufficient with regard to a desired post-processing process among a plurality of post-processing processes for the first measurement data, the modified set of control parameters modified based on an automatic inspection of a set of control parameters with aid of an analysis of the first measurement data using defined criteria, the desired post-processing process including a data modification operation or a data analysis operation, the defined criteria including at least one of a post-processing capacity of the desired post-processing process or identification of at least one image characteristic associated with the post-processing capacity;
an analysis unit to determine whether the first measurement data is insufficient with regard to the desired post-processing process for the first measurement data by automatically analyzing the first measurement data using a neural network based on the defined criteria, the neural network being trained based on reference measurement data of reference objects of examination, and the reference measurement data including positive reference measurement data determined to provide a sufficient result image when processed by the desired post-processing process; and
a post-processing unit to perform the desired post-processing process on the second measurement data.

26. A medical imaging system comprising:
the control device of claim 25; and
the medical imaging modality.

27. The control device of claim 25, further comprising:
a modification unit to modify the set of control parameters to obtain the modified set of control parameters.

28. A medical imaging system comprising:
the control device of claim 27; and
the medical imaging modality.

29. The control device of claim 25, wherein the post-processing unit is configured to perform the desired post-processing process using the first measurement data in response to determining that the first measurement data is sufficient with regard to the desired post-processing process.

30. A medical imaging system comprising:
the control device of claim 29; and
the medical imaging modality.

31. A control device comprising:
an acquisition unit to
record first measurement data of an object of examination, the first measurement data determined via a medical imaging modality, and
record second measurement data of the object of examination, the second measurement data obtained via the medical imaging modality using a modified set of control parameters in response to determining that the first measurement data is insufficient with regard to a desired post-processing process among a plurality of post-processing processes for the first measurement data, the modified set of control parameters modified based on an automatic inspection of a set of control parameters with aid of an analysis of the first measurement data using defined criteria, the desired post-processing process including a data modification operation or a data analysis operation, the defined criteria including at least one of a post-processing capacity of the desired post-processing process or identification of at least one image characteristic associated with the post-processing capacity;
a memory configured to store computer-readable instructions; and
one or more processors configured to execute the computer-readable instructions to
determine whether the first measurement data is insufficient with regard to the desired post-processing process for the first measurement data by automatically analyzing the first measurement data using a neural network based on the defined criteria, the neural network being trained based on reference measurement data of reference objects of examination, the reference measurement data including positive reference measurement data determined to provide a sufficient result image when processed by the desired post-processing process, and
perform the desired post-processing process using the second measurement data.

32. A medical imaging system comprising:
the control device of claim 31; and
the medical imaging modality.

33. The control device of claim 31, wherein the one or more processors are configured to execute the computer-readable instructions to modify the set of control parameters to obtain the modified set of control parameters.

34. The control device of claim 33, wherein the one or more processors are configured to execute the computer-readable instructions to perform the desired post-processing process using the first measurement data in response to determining that the first measurement data is sufficient with regard to the desired post-processing process.

35. The control device of claim 31, wherein the one or more processors are configured to execute the computer-readable instructions to perform the desired post-processing process using the first measurement data in response to determining that the first measurement data is sufficient with regard to the desired post-processing process.

* * * * *